United States Patent [19]

Lillwitz

[11] Patent Number: 4,754,064

[45] Date of Patent: Jun. 28, 1988

[54] PREPARATION OF CYCLOHEXANE DICARBOXYLIC ACIDS

[75] Inventor: Lawrence D. Lillwitz, Glen Ellyn, Ill.

[73] Assignee: Amoco Corporation, Chicago, Ill.

[21] Appl. No.: 544,725

[22] Filed: Oct. 24, 1983

[51] Int. Cl.[4] ............................................. C07C 61/09
[52] U.S. Cl. ....................................... 562/509; 260/690
[58] Field of Search ................ 562/509; 585/266, 269; 260/690

[56] References Cited

U.S. PATENT DOCUMENTS

| | | | |
|---|---|---|---|
| 2,675,390 | 4/1954 | Rosenblatt | 562/509 X |
| 2,828,335 | 3/1958 | Ferstandig et al. | 562/509 |
| 2,888,484 | 5/1959 | Dehm et al. | 562/509 |
| 3,326,972 | 6/1967 | Schenk et al. | 562/509 |
| 3,420,908 | 1/1969 | Sherk et al. | 585/269 X |
| 3,444,237 | 5/1969 | Jaffe | 560/127 |

FOREIGN PATENT DOCUMENTS 0764502  8/1967  Canada ................................ 585/266

OTHER PUBLICATIONS

*J. Organic Chemistry*, vol. 31, 1966, pp. 3438–3439; Freifelder et al.

Primary Examiner—Donald B. Moyer
Assistant Examiner—Patricia M. Scott
Attorney, Agent, or Firm—James R. Henes; William H. Magidson; Ralph C. Medhurst

[57] ABSTRACT

Cyclohexane dicarboxylic acids are prepared by hydrogenating phthalic acids in presence of a rhodium catalyst wherein a portion of the product stream is isolated and recycled to the reactor.

11 Claims, 1 Drawing Sheet

COMPARISON OF ISOPHTHALIC ACID REDUCTION RATES

PREPARATION OF CYCLOHEXANE DICARBOXYLIC ACIDS

FIELD OF THE INVENTION

The field of this invention relates to an improved process for the preparation of cyclohexane dicarboxylic acids by the hydrogenation of phthalic acids in the presence of a rhodium catalyst wherein a portion of the product stream is isolated and returned to the reactor to obtain an increased reaction rate at a low catalyst to phthalic acid weight ratio.

BACKGROUND OF THE INVENTION

It has long been known that cyclohexane dicarboxylic acids can be prepared by the hydrogenation of phthalic acids over a suitable catalyst. For example, Freifelder, et al., *J. Org. Chem.*, 31, 3438 (1966) teaches the low pressure hydrogenation of benzene polycarboxylic acids using a rhodium catalyst supported on carbon or on alumina. Good yields were obtained of the corresponding cyclohexane dicarboxylic acids by hydrogenation in aqueous solution of phthalic, isophthalic and terephthalic acids at reaction temperatures of 60°–70° C. and pressures less than 3 atmospheres. At this temperature range, sufficient starting acid dissolved to allow uptake of hydrogen to proceed at a good rate. For example, pyromellitic acid was hydrogenated to cyclohexane-1,2,4,5-tetracarboxylic acid with 75% yield with uptake of hydrogen complete in 1.5 hours. Yields from respective acids were: cyclohexane-1,2-dicarboxylic acid 93%, cyclohexane-1,3-dicarboxylic acid 96% and cyclohexane-1,4-dicarboxylic acid over 90%. However, the process of Freifelder required extremely high concentrations of 5% rhodium-on-carbon catalysts. Requirements were 5 grams of catalyst to 12.7 grams of pyromellitic acid, and 4.0 grams of 5% rhodium on alumina per 8.3 g (0.05 mole) of the other dibasic acids although in some instances 2.0 grams of 2.5% rhodium on alumina were used as catalyst. Freifelder noted that the success of the hydrogenation reaction could be more dependent on the water solubility of the reduction product than that of the starting acid. Freifelder was accordingly suggesting that choice of solvent could be determining the reaction rate.

Other previous teachings relate to hydrogenation of cyclic compounds. U.S. Pat. No. 2,675,390 teaches the hydrogenation of cyclic compounds at room temperature and atmospheric pressure using catalysts comprising rhodium supported upon a suitable carrier which can be carbon or alumina. Examples of cyclic compounds are benzene, toluene, benzoic acid, phthalic acid, furane, fuoric acid, phenol pyrrole, and hydroquinone in a suitable solvent, water or acetic acid. Yields of practically 100% were obtained by hydrogenating pyrroles. High concentrations of catalyst to reactant material were required. For example, as high as 1 gram of catalyst was required per 0.5 cc of diethyl phthalate in acetic acid. U.S. Pat. No. 2,828,335 teaches hydrogenation of phthalic acid salts in water in the presence of a catalyst containing ruthenium in an amount of from 0.01 to 5 weight percent at a temperature within the range of from atmospheric to 250° C. Yields from sodium isophthalate were 90 to 92 mole percent as the hexahydroisophthalic acid using low concentrations of ruthenium catalyst. Example 7 teaches a slurry of 156 grams of sodium isophthalate in 210 grams of water in the presence of 1.01 grams of ruthenium oxide. A temperature of 110° C. was held for 4.7 hours to complete the hydrogenation. U.S. Pat. No. 2,888,484 teaches use of an inert liquid medium in which a phthalic acid, e.g., terephthalic acid, is at least partially soluble under reaction conditions of 150° C. to 300° C. and pressure greater than 1000 psig. Hexahydroterephthalic acid was obtained in yields of 93% at a temperature of 180° C. and reaction pressure of 5000 psi wherein the terephthalic acid:catalyst weight ratio was 10:1. The catalyst is palladium or ruthenium on carbon or silica gel. A 5% rhodium-on-carbon catalyst at 300° C. and 5000 psig for 4½ hours gave a conversion of 100% but a yield of only 38%. At less drastic conditions, the yield was lower. U.S. Pat. No. 3,444,237 teaches hydrogenation of an alkali salt of trimellitic anhydride to yield mixed isomers of cyclohexane-1,2,4-tricarboxylic acid. Catalyst is ruthenium on activated carbon at a rate of 2 to 25 grams of catalyst per mole of trimellitic anhydride. Examples I and II teach use of 10 grams of catalyst per 200 grams (1.04 mole) of trimellitic anhydride.

Accordingly, previous investigators have determined that phthalic acids can be catalytically hydrogenated in the presence of a solvent wherein catalyst:reactant weight ratio can be in the range from 1:2 to 1:10 or higher, depending upon whether rhodium, ruthenium or palladium is used as the catalyst. Rhodium, palladium and ruthenium on activated carbon or silica have been the catalysts of choice, depending on the phthalic acid to be hydrogenated. The solution has been of water or acetic acid. Reaction rates have been increased by increasing catalyst concentration relative to reactant, although Friefelder suggested that choice of solvent could be a factor in success of the reaction.

Increasing reaction rates by increasing the amount of catalyst to reactant in a commercial process using a rhodium, palladium or ruthenium catalyst increases the economic cost of the process and can result in the process being of little economic value. Consequently, an improved process is very much desired for hydrogenating phthalic acids to cyclohexane dicarboxylic acids wherein rhodium catalyst concentration relative to parts of phthalic acid is less than previously taught, reaction rates are increased, and conversion and selectivity are both nearly 100% to obtain yields of approximately 100%.

My invention is an improvement in the preparation of cyclohexane dicarboxylic acids wherein reaction rates are increased by isolating a portion of the product stream and returning the said portion to the reactor. I have discovered that the increased concentration of product in the reactor increases significantly the reaction rate both in terms of rate of phthalic acid conversion and cyclohexane dicarboxylic acid production. It has also been found that in continuous operation, under conditions wherein the used catalyst is recycled, the used catalyst retains its catalytic activity for long periods of use.

It is accordingly an object of this invention to provide a process for the hydrogenation of phthalic acids wherein an increased rate of reaction is obtained without use of added quantities of catalyst over rates obtained by previously-taught processes using rhodium-on-carbon catalysts. It is also an object of this invention to provide a process for hydrogenation of phthalic acids wherein the catalyst is recycled for long periods of time without loss of activity. It is also an object of this invention to provide a process for hydrogenation of phthalic acids wherein a reduced weight ratio of rhodium-on-carbon catalyst to phthalic acid is used versus weight ratios of catalyst to phthalic acid in previously taught processes. Other objects will appear in further reading.

SUMMARY OF THE INVENTION

Disclosed is an improved process for hydrogenation of phthalic acids in solution in the presence of a supported rhodium catalyst wherein the reaction rate is improved over that previously taught by recycle of a product solution containing at least 5 (wt)% reaction product and the catalyst:acid weight ratio is from about 1:20 to about 1:50 for isophthalic acid and from about 1:3 to about 1:5 for terephthalic acid.

DETAILS OF THE INVENTION

It has now been discovered that phthalic acid, isophthalic and terephthalic, can be hydrogenated with an improved reaction rate at a temperature within the range of from about 90° to 140° C. and hydrogen pressures of from about 500 to 1500 psig to 1,2-, 1,3- and 1,4-cyclohexane dicarboxylic acid in good yield in aqueous solution in the presence of a supported rhodium catalyst wherein catalyst:acid weight ratios are from about 1:20 to about 1:50 for isophthalic, from about 1:3 to about 1:5 for terephthalic, by recycle of a portion of the solution containing approximately 5 to 25 (wt)% reaction product. Reactions using catalyst metals other than rhodium require a higher reaction temperature and reaction rates are slower, requiring additional time to complete the reaction, and product yields can be lower. Aromatic polycarboxylic acids such as terephthalic acid require a higher concentration of catalyst and higher catalyst loading. Hydrogenation of terephthalic acid in presence of a rhodium catalyst also results in more by-products than does hydrogenation of isophthalic acid in presence of a rhodium catalyst. Orthophthalic acid can also be hydrogenated in presence of a rhodium catalyst with recycle of a portion of the reaction product.

The role of the recycle product in the reaction mixture has not been entirely determined, but apparently the greater the concentration of the reaction product the greater is the rate at which the phthalic acid is hydrogenated to the hexahydrophthalic acid product. It is postulated that the presence of cyclohexane dicarboxylic acid in the reactant solution may aid in solubilizing hydrogen or the phthalic acid in the solution. Hydrogenation being a surface phenomenon upon the surface of the catalyst, the hydrogenation reaction of hydrogen and phthalic acid may be aided also by the presence of cyclohexane dicarboxylic acid on the surface of the catalyst.

Figure 1:
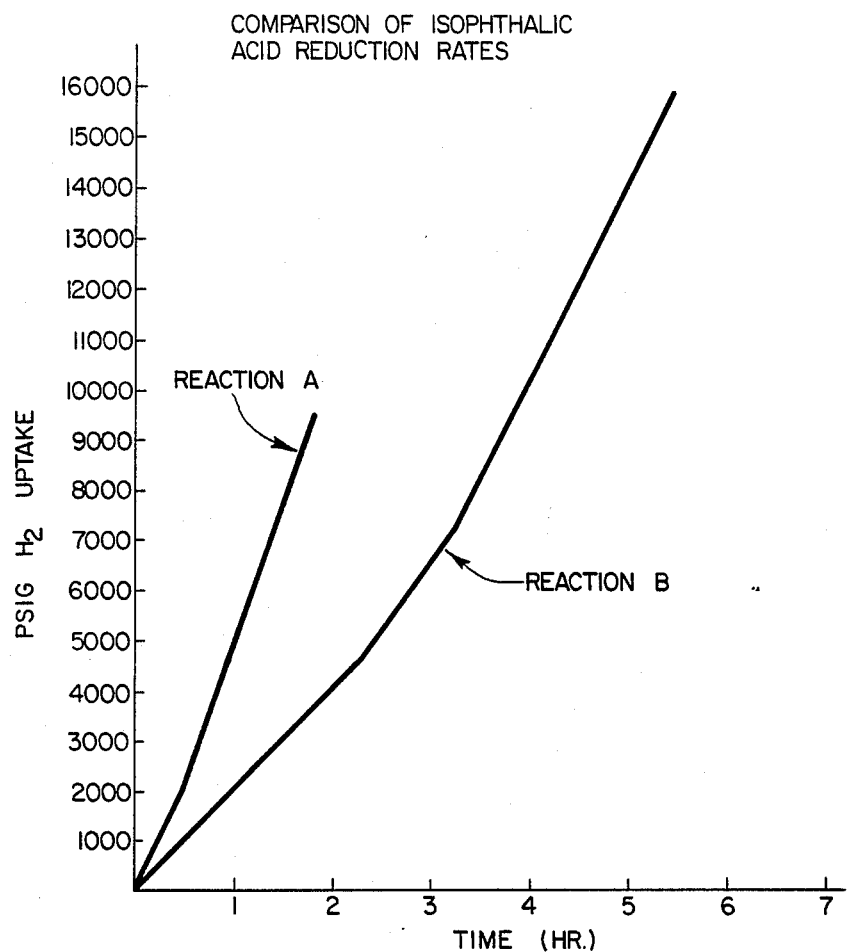
FIG. 1 is a chart of isophthalic acid reaction rates versus time of two reactions, Reaction A (Example II), wherein recycle product was returned to the reactor, and Reaction B (Example I), wherein recycle product was not present and reaction product was not removed from the reactor until end of the batch run.

FIG. 1 is a chart of isophthalic acid reaction rate versus time of two reactions, Reaction A wherein recycle product was returned to the reactor, and Reaction B wherein recycle product was not present and reaction product was not removed from the reactor until end of the batch run.

Rate of reaction of Reaction A increased sharply at the beginning and stabilized between ½ and 1 hour. Rate of reaction of Reaction B increased as product remained in the reactor, increasing to a maximum rate toward the end of the batch reaction, during the last 2 hours of the reaction.

Figure 2:
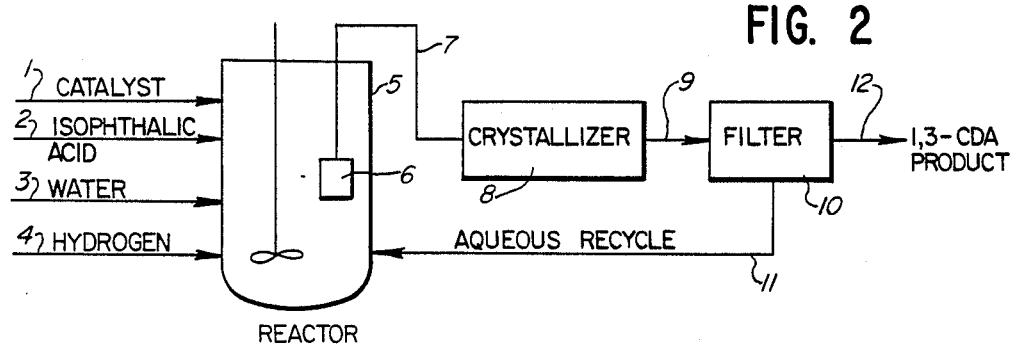
FIG. 2 is a schematic flow diagram of one embodiment of the claimed invention.

Referring to FIG. 2, in the preparation of 1,3-cyclohexane dicarboxylic acid, catalyst, isophthalic acid and water are introduced into reactor 5 by lines 1, 2 and 3. Hydrogen is introduced into the reactor by line 4. Catalyst is filtered from product by filter 6. Product is transferred from reactor 5 by line 7 into crystallizer 8 wherein temperature of the aqueous solution containing product, 1,3-cyclohexane dicarboxylic acid, is reduced to 60° C. or less. Slurry from crystallizer 8 is passed to filter 10 by line 9. Aqueous mother liquor containing at least 5 (wt)% of 1,3-cyclohexane dicarboxylic acid is recycled to reactor 5 by line 11. Product is removed from filter 10 by line 12.

For the purposes of this invention, the phthalic acid and the hydrogen gas may be contacted with the supported rhodium catalyst in any suitable manner known to those skilled in the art. For example, the reactants may be continuously introduced into a reaction zone containing the rhodium catalyst. Also, the process may be effected in a batchwise manner. The product of hydrogenation is then recovered by filtering or, by fractional distillation, by the use of selective solvents, or in any other well-known way. The phthalic acid to be treated is dissolved or suspended in a suitable polar solvent. Strongly polar solvents such as ethyl acetate, water, and tetrahydrofuran are preferred. The amount of solvent does not influence the reaction except when causing extreme dilution.

Phthalic acids are typically slightly soluble in water. Feed to hydrogenation in water or other solutions accordingly is in the form of a slurry of the respective aromatic acid at such a concentration to produce a concentrated solution of product at room temperature.

For example, isophthalic acid is only slightly soluble in water, 0.01 parts in 100 parts of water at 25° C. Consequently, isophthalic acid is hydrogenated as a slurry of 45 parts acid to 100 parts of water. After hydrogenation the catalyst of supported rhodium is filtered from the solution of the product at elevated temperature (60°–70° C.). The filtered reactor effluent is chilled to crystallize out the hydrogenated acid product. The product is a mixture of cis and trans isomers.

Use of a water slurry in hydrogenating isophthalic acid offers the advantage that 1,3-cyclohexane dicarboxylic acid (1,3-CDA) is soluble in water at 60° C. Catalyst to isophthalic acid weight ratio is from about 1:20 to about 1:50. Upon cooling to room temperature, approximately 80% of the 1,3-CDA present as solute at 60° C. precipitates out, thus permitting easy recovery of product.

Use of ethyl acetate in hydrogenating terephthalic acid also offers the advantage that 1,4-cyclohexane dicarboxylic acid (1,4-CDA) is soluble in ethyl acetate at reaction temperature of 110°–115° C. Catalyst to terephthalic acid weight ratio is from about 1:3 to about 1:5. Upon cooling to room temperature, the product, cis/trans 1,4-cyclohexane dicarboxylic acid, precipitates.

Use of a water slurry in hydrogenating orthophthalic acid offers the advantage that 1,2-cyclohexane dicarboxylic acid (1,2-CDA) is soluble in the trans form in hot water and slightly soluble in the cis form in hot water. Upon cooling to room temperature, the product, the cis/trans 1,2-cyclohexane dicarboxylic acid, precipitates.

The support for the rhodium may be in the form of pellets, granules or powder and it consists of preferably of dehydrated alumina, in particular activated alumina, or activated carbon. Other carriers that may be used are dehydrated zirconium dioxide, chromium oxide, kieselguhr, bentonite, asbestos, dehydrated silica gel, and the like. However, for the purposes of this invention it has been found that the carrier or support is preferably alumina or activated carbon.

The supported catalyst is prepared in any suitable manner, e.g., by treating the carrier with a solution of suitable rhodium compound and then reducing such compound to rhodium metal. Care should be taken not to heat the carrier or the rhodium compound to excessive temperatures and, hence, thermal decomposition of the rhodium compound is preferably avoided.

Reaction temperature is within the range of from about 90° C. to 140° C., preferably from about 100° C. to 110° C. Use of a lower temperature, within the range of from 65° C. to 90° C., results in a slower reaction rate. Below 65° C., 1-3 CDA precipitates from an aqueous solution. Above 140° C., selectivity to 1,3-cyclohexane dicarboxylic acid falls and mono carboxylic acids are produced. Hydrogen pressure is within the range of from about 300 to 1800 psig, preferably from about 500 to 1500 psig.

The time required for essentially complete hydrogenation of the phthalic acids in the process of the instant invention varies with the phthalic acid and the catalyst:phthalic acid weight ratio employed. In the hydrogenation of isophthalic acid, the reaction rate at 110°-111° C. using the process of the instant invention results in a reduction of from 5½ hours to approximately two hours using a catalyst:acid weight ratio of less than 1:20. In the hydrogenation of terephthalic acid, a catalyst:acid weight ratio greater than 1:20 but less than 1:10 at 130°-140° C., after 24 hours, resulted in very little product. Increasing the catalyst:acid weight ratio to greater than 1:4 but less than 1:3 and without recycle of 1,4-CDA resulted in a completed reaction in 4 hours at 110°-115° C. Additional catalyst permitted the lower reaction temperature. Addition of 1,4-CDA of about 5 (wt)% of terephthalic acid present with a catalyst:acid weight ratio of greater than 1:4 and less than 1:3 at 110°-111° C. resulted in a completed reaction in 2 hours. Increasing the amount of 1,4-CDA to about 25 (wt)% of the terephthalic acid present resulted in a completed reaction in less than one hour.

In summary, the invented process for the preparation of cyclohexane dicarboxylic acid comprises the steps of (a) hydrogenating a phthalic acid in a suitable solvent in the presence of a supported rhodium catalyst at a temperature within the range of from about 90° C. to 140° C., preferably from about 100° C. to abou 130° C. and a pressure of from about 300 to 1800 psig, preferably from about 500 to 1500 psig, (b) filtering the catalyst from reactor effluent at a temperature within the range of from about 15° C. to about 110° C., (c) crystallizing the filtrate at a temperature within the range of from about 15° C. to about 60° C., (d) recycling to the reactor the mother liquor containing at least 5 (wt)% of cyclohexane dicarboxylic acid.

The invention will be illustrated by reference to the following specific examples.

EXAMPLE I

The following example illustrates that isophthalic acid is hydrogenated in presence of a 5 (wt)% rhodium-on-carbon catalyst wherein catalyst:acid weight ratio is less than 1:20 but that an extended reaction time, 5½ hours is required.

1334 g of isophthalic acid, 2000 cc's of distilled water and 40 g of 5 (wt)% rhodium-on-carbon were charged to a one-gallon stainless steel, stirred autoclave. The temperature was 110°-111° C., and hydrogen pressures ranged between 1000-1500 psig. The reaction was complete in 5½ hours. Hydrogen uptake was measured every 15 minutes for the first 2½ hours and then at each 500 psig incremental increase in hydrogen pressure for 3½ hours. Product isolation and workup were as follows: the reactor contents were filtered at 60° C. to recover only the 5% rhodium-oncarbon catalyst. The aqueous filtrate was stirred at room temperature overnight and then filtered to recover 1235 g of dry 1,3-cyclohexane dicarboxylic acid. Theoretical yield based on the fresh-charged isophthalic acid (1334 g) was 1381 g. The remaining 146 g of product saturated the aqueous filtrate.

EXAMPLE II

The following illustrates the improved reaction rate obtained by use of recycle aqueous filtrate. Reaction time was reduced from 5½ hours, as in Example I, to 2 hours. Catalyst:acid weight ratio of greater than 1:20 was not required, as is taught in previous art, to obtain an increased reaction rate.

1100 g of isophthalic acid, 1250 ml of recycle aqueous filtrate from Example I, 750 ml of fresh distilled water and the 40 g of used 5 (wt)% rhodium-on-carbon catalyst from Example I were charged to a one-gallon stainless steel, stirred autoclave. The temperature and pressure were exactly the same as those used in Example I. Hydrogen uptake was measured approximately every 30 minutes for the first 1½ hours. The reaction was complete in less than 2 hours. The reactor contents were worked up exactly as in Example I to give 1118 g of dry 1,3-cyclohexane dicarboxylic acid. Theoretical yield based on the fresh-charged isophthalic acid (1100 g) was 1138 g, approximately 98%. The remaining 20 grams of product saturated the additional fresh water added to the reactor.

EXAMPLE III

The following example illustrates the prolonged catalyst activity obtained by the instant process. Catalyst:acid weight ratio was less than 1:20.

Example II was scaled up to produce approximately 50-lb. batches of 1,3-cyclohexane dicarboxylic acid in a 25-gallon stainless steel, stirred autoclave. 62 lbs. of isophthalic acid, recycle water filtrate, 10 gallons, from a previous run, 5 gallons of fresh water and 1000g of used 5 (wt)% rhodium-on-carbon catalyst were charged to the above autoclave. The temperature was 100° C. and the hydrogen pressure ranged between 1000-1500 psig. The reaction was complete in approximately 2 hours. The reaction workup was the same as in Example I. Several runs of this scale produced 500 lbs. of 1,3-cyclohexane dicarboxylic acid using the same 1000 g of the rhodium-on-carbon catalyst. The catalyst remained very active.

EXAMPLE IV

The following example illustrates that terephthalic acid in ethyl acetate in presence of low levels of 5 (wt)% rhodium-on-carbon catalyst undergoes little hydrogenation wherein catalyst:acid weight ratio is greater than 1:20 but less than 1:10. 1,4-cyclohexane dicarboxylic acid is soluble in ethyl acetate at 130°-140° C.

500 g of terephthalic acid, 2700 cc's of ethyl acetate and 37 g of 5 (wt)% rhodium-on-carbon were charged to a one-gallon stainless steel, stirred autoclave. The temperature was 130°-140° C., and hydrogen pressure ranged between 1000-1500 psig. After approximately 24 hrs. a reaction product aliquot was isolated and analyzed to show very little hydrogenation.

EXAMPLE V

The following illustrates that terephthalic acid can be hydrogenated at 110°-115° C. but that increased quantities of catalyst are required versus the conditions of Example IV. A catalyst:acid weight ratio, greater than 1:4 and less than 1:3, was required to complete the reaction in 4 hours. Solubility of product was not determined to be a factor in success of the reaction.

To the reaction mixture (product) of Example IV was added 98.6 g of 5 (wt)% rhodium-on-carbon. The temperature range was 110°-115° C., and the hydrogen pressure ranged between 1000-1500 psig. The reaction was complete in 4 hrs. The reaction product work up consisted of filtering the catalyst from the reaction product at boiling ethyl acetate temperatures, and washing the catalyst many times with boiling ethyl acetate to solubilize the trans 1,4-CDA. The ethyl acetate filtrate and washings were cooled to room temperature to recover the product, cis/trans 1,4-cyclohexane dicarboxylic acid.

EXAMPLE VI

The following example illustrates that presence of hydrogenated terephthalic acid product of about 5 (wt)% of terephthalic acid present increases hydrogenation rate of terephthalic acid. Catalyst:acid ratio was greater than 1:4 but less than 1:3.

400 g of terephthalic acid, 28 g of cis/trans 1,4-cyclohexane dicarboxylic acid (7 (wt)% of terephthalic acid), 2200 ml of fresh distilled water and 135 g of 5 (wt)% rhodium-on-carbon catalyst were charged to a one-gallon stainless steel, stirred autoclave. The temperature, 110°-111° C., and pressure, 1000-1500 psi gauge, were exactly the same as in Example V. The reaction was complete in 2 hrs. The reaction contents were filtered at 90°-100° C., and the catalyst filter cake was washed several times with boiling water to solubilize trans 1,4-CDA. The filtrate and washings were cooled to room temperature to recover the product, cis/trans 1,4-cyclohexane dicarboxylic acid.

EXAMPLE VII

The following example illustrates that increased presence of hydrogenated product of about 25 (wt)% of hydrogenated phthalic acid increases hydrogenation rate of phthalic acid and reduces reaction time. Reaction rate is greater than when about 5 (wt)% of hydrogenated phthalic acid product is present.

350 g of terephathalic acid, 80 g of cis/trans 1,4-cyclohexane dicarboxylic acid, approximately 23 (wt)% of terephthalic acid present, 2200 ml of fresh distilled water and the rhodium-on-carbon catalyst used in Example VI were charged to a one-gallon stainless steel, stirred autoclave. The temperature and pressure were exactly the same as in Example VI. The reaction was complete in 50 minutes and the reaction product was worked up exactly the same as in Example VI.

What is claimed is:

1. An improved process for preparation of a cyclohexane dicarboxylic acid from a phthalic acid reactant which comprises the steps of (a) hydrogenating said phthalic acid reactant in a polar solvent in the presence of a supported rhodium catalyst at a temperature within the range of 90° C. to 140° C. and a pressure of from 300 to 1800 psig, (b) filtering the catalyst from reactor effluent at a temperature within the range of from 15° C. to 110° C., (c) crystallizing the filtrate at a temperature of from 15° C. to 60° C., (d) the improvement in combination therewith comprising recycling back to the reactor mother liquor containing from about 5 (wt)% to about 25 (wt)% reaction product based on the weight of the phthalic acid reactant.

2. The process of claim 1 wherein said solvent is selected from the group consisting of water, ethyl acetate and tetrahydrofuran.

3. The process of claim 1 wherein said phthalic acid is isophthalic acid, said solvent is water, said supported rodium catalyst is 5 (wt)% rhodium-on-carbon and catalyst:isophthalic acid weight ratio is from about 1:20 to about 1:50.

4. The process of claim 1 wherein said phthalic acid is terephthalic acid, said solvent is ethyl acetate, said supported rhodium catalyst is 5 (wt)% rhodium-oncarbon and catalyst:terephthalic acid weight ratio is from about 1:3 to about 1:5.

5. The process of claim 1 wherein said phthalic acid is present in the form of an aqueous slurry.

6. The process of claim 1 wherein said temperature is within the range of from about 100° C. to about 125° C. and pressure is from 500 to 1500 psig.

7. The process of claim 1 wherein support of said supported catalyst is selected from the group consisting of activated carbon, alumina, dehydrated zirconium oxide, chromium oxide, kieselguhr, bentonite, asbestos and silica gel.

8. The process of claim 1 wherein support of said supported catalyst is selected from the group consisting of activated carbon and alumina.

9. The process of claim 1 wherein said mother liquor recycled back to said reactor contains from about 5 (wt)% to about 25 (wt)% reaction product.

10. The process of claim 1 wherein said process is a batch process.

11. The process of claim 1 wherein said process is a continuous process.

* * * * *